United States Patent
Trudeau et al.

(10) Patent No.: US 7,452,360 B2
(45) Date of Patent: *Nov. 18, 2008

(54) METHOD AND APPARATUS FOR CLAMPING SURGICAL WIRES OR CABLES

(75) Inventors: Jeffrey L. Trudeau, Marquette, MI (US); Thomas S. Kilpela, Marquette, MI (US); Brian P. Janowski, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/994,088

(22) Filed: Nov. 14, 2001

(65) Prior Publication Data

US 2002/0032450 A1    Mar. 14, 2002

Related U.S. Application Data

(63) Continuation-in-part of application No. 09/442,293, filed on Nov. 19, 1999, now Pat. No. 6,378,289.

(51) Int. Cl.
*A61B 17/56* (2006.01)
*A61B 17/58* (2006.01)

(52) U.S. Cl. .......................... 606/103; 606/74
(58) Field of Classification Search .............. 606/74, 606/83, 103; 24/134 KB, 134 R; 254/199, 254/230, 231, 232
See application file for complete search history.

(56) References Cited

U.S. PATENT DOCUMENTS

| | | | | |
|---|---|---|---|---|
| 2,049,361 A | * | 7/1936 | Ericsson ............. 606/103 |
| 3,824,653 A | * | 7/1974 | Sholler ............. 24/134 KB |
| 4,881,303 A | | 11/1989 | Martini |
| 4,912,817 A | | 4/1990 | Sandreid |
| 4,966,600 A | | 10/1990 | Songer et al. |
| 5,083,350 A | * | 1/1992 | Sandreid ............. 24/134 R |
| 5,312,410 A | | 5/1994 | Miller et al. |
| 5,395,374 A | | 3/1995 | Miller et al. |
| 5,395,375 A | | 3/1995 | Turkel et al. |
| 5,449,361 A | | 9/1995 | Preissman |
| 5,531,297 A | * | 7/1996 | Pipan ................ 188/65.1 |
| 5,569,253 A | | 10/1996 | Farris et al. |
| 5,788,351 A | | 8/1998 | Prunty et al. |
| 5,788,697 A | | 8/1998 | Kilpela et al. |
| 5,855,251 A | * | 1/1999 | Deuer .................. 182/5 |
| 5,902,305 A | * | 5/1999 | Beger et al. ........... 606/103 |
| 5,935,130 A | | 8/1999 | Kilpela et al. |
| 6,378,289 B1 | * | 4/2002 | Trudeau et al. ........ 606/103 |
| 6,505,384 B1 | * | 1/2003 | Renton et al. ......... 24/134 R |

* cited by examiner

*Primary Examiner*—Pedro Philogene
(74) *Attorney, Agent, or Firm*—Fitch, Even, Tabin & Flannery (57) ABSTRACT

Disclosed is a clamp for securing cables or other elongate members used in surgical fastening procedures. The clamp advantageously applies a clamping force to the cable without direct contact with the cable, thereby reducing abrasion and shear forces applied to the cable. The disclosed clamps have a saddle member, platen or both that are movably mounted with respect to the housing and a lever, in cooperation with a cam surface, that allows the saddle member, platen or both to selectively clamp the cable. The lever may have several locking positions to provide optimum clamping force to different sized cables.

13 Claims, 13 Drawing Sheets

METHOD AND APPARATUS FOR CLAMPING SURGICAL WIRES OR CABLES

This is a continuation-in-part application of U.S. patent application Ser. No. 09/442,293 filed Nov. 19, 1999, now U.S. Pat. No. 6,378,289 from which priority is claimed and which is incorporated herein by reference in its entirety.

FIELD OF THE INVENTION

The invention relates generally to surgical methods and apparatus for clamping cables or wires. More particularly, the invention relates to methods and apparatus for clamping cables, wires or other elongate members used in orthopedic surgical techniques.

DESCRIPTION OF THE PRIOR ART

Surgical cables and wires are now used extensively in orthopedic surgery for securing bones and bone fragments in place and for fastening surgical implements to bones. Typically, surgical cables are implanted using tensioning devices, which apply tension to a cable looped around the bone, and crimps that are deformed to clamp the cable loop in place.

The prior art is typified by U.S. Pat. No. 5,395,374 to Miller et al, the entire writing of which is incorporated herein by reference. The disclosed technique involves the use of a small lever-action cable clamp located along the cable between the crimp and the tensioning tool. A first cable may be provided with a pre-final amount of tension and then the cable clamp operated to secure the first cable in the pre-final position. The tensioning tool may then be removed from the first cable and used in conjunction with another cable clamp, to apply tension to a second cable. This technique permits the readjustment of the tension on the cables used in an orthopedic application.

Cable clamps like those of the prior art incorporate a cam lever that bears directly on the cable surface. Thus, as the cam lever is operated to clamp the cable, the clamping force is applied to a relatively small area of the cable surface and the cable is subjected to potentially damaging shear and compressive forces. This may result in local weakening of the cable, which is undesirable especially since the cable may be in place for long periods of time and subject to repetitive stresses and any weakened portion will represent the potential for failure of the cable. It would therefore be desirable to provide an improved cable clamp that can be used to temporarily clamp a cable without subjecting the cable to potentially damaging localized stresses.

Another problem with cable clamps of the prior art is that they do not provide for efficient and risk-free operation with a variety of different sized cables. Different sized cables are employed in surgical operations, depending on the particular application. Cable clamps like the one disclosed by Miller and described above, are configured to have only an open and closed position, with the closed position applying the maximum clamping force to the cable. When used with larger cable diameters, prior art devices may apply excessive and damaging forces to the cable when the cam is moved to the clamping position. It would therefore be desirable to provide a cable clamping device having a single design that may be used to efficiently and safely clamp cables having different diameters or lateral dimension.

Yet another shortcoming of prior art cable clamps is that they do not provide stable locking positions or positive indication to a surgeon as to when suitable clamping force has been applied to the clamped cable. For example, prior art devices like the one described by Miller use a cam lever having a smooth cam surface without predefined locking positions. Thus, a physician must rely only on the tactile sensation of continuously increasing forces applied to the cam lever to determine when sufficient clamping force is applied to the cable. It would therefore be desirable to provide a cable clamp which has at least one pre-defined locking position and which provides a positive tactile indication to a surgeon that sufficient yet safe clamping force has been applied to the clamped cable. It would further be desirable to provide such stable locking positions and positive tactile indication for more than one size of cable to be used with the cable clamp.

BRIEF SUMMARY OF THE INVENTION

The aforementioned problems are addressed by the present invention, which in an exemplary embodiment provides a clamping device incorporating a cable housing, a cable bore defined therein and a pivotable lever to move a clamping member relative to the housing. In various aspects of the invention, the clamping member is defined by a saddle member and/or a platen adapted to move relative to the housing for clamping an elongate member within the cable housing. The saddle member, platen or housing may further be equipped with an engaging surface adapted to enhance the clamping ability of the device by, for example, redirecting the elongate member to a non-linear path at the point of clamping. The pivotable lever cooperates with a lever interface surface so that movement of the lever results in movement of the clamping member to engage the elongate member within the housing. In other aspects of the invention, the face of the lever may be a faceted cam surface or a generally smooth, oblong lobe with or without one or more facets, while the lever interface surface, may be a generally smooth surface or a cam surface having at least two discrete surface areas. In this way, the combination of lever and lever interface surface further cooperate to define locking positions associated with optimal clamping forces applied to elongate members of various sizes.

Because the lever of the present invention does not act directly on the surface of the elongate member, and because the saddle member and platen apply force in a direction that is generally transverse to the elongate member, the elongate member may be clamped in a safe and efficient manner without potentially damaging compressive or shear forces. Clamping a tensioned cable through a clamp with an end to end linear aperature requires that all normal forces on the cable be generated by the clamp closing down on the cable. However, a tensioned cable through a clamp with an undulating or otherwise non-linear aperature can generate normal force on the cable by simply applying tension to the cable. With tension, the cable attempts to straighten and consequently applies normal forces to the obstructing internal surfaces of the clamp. These cable tension induced normal forces reduce the normal forces required to be generated by the clamp body through action of the lever.

The present invention further overcomes limitations of the prior art by providing a plurality of locking positions that enable a surgeon to determine by a positive tactile indication that sufficient clamping force has been applied to the elongate member. The dimensions of the lever face and lever interface surface correspond to optimal clamping positions for different diameter elongate members that can be used with the clamping device. Thus, as the lever is rotated to a pre-defined locking position, the surgeon is given a tactile indication as to the relative clamping force being applied to the elongate member, and a single cable clamp design can be used with more than one size of cable.

DETAILED DESCRIPTION OF THE INVENTION

Figure 1:
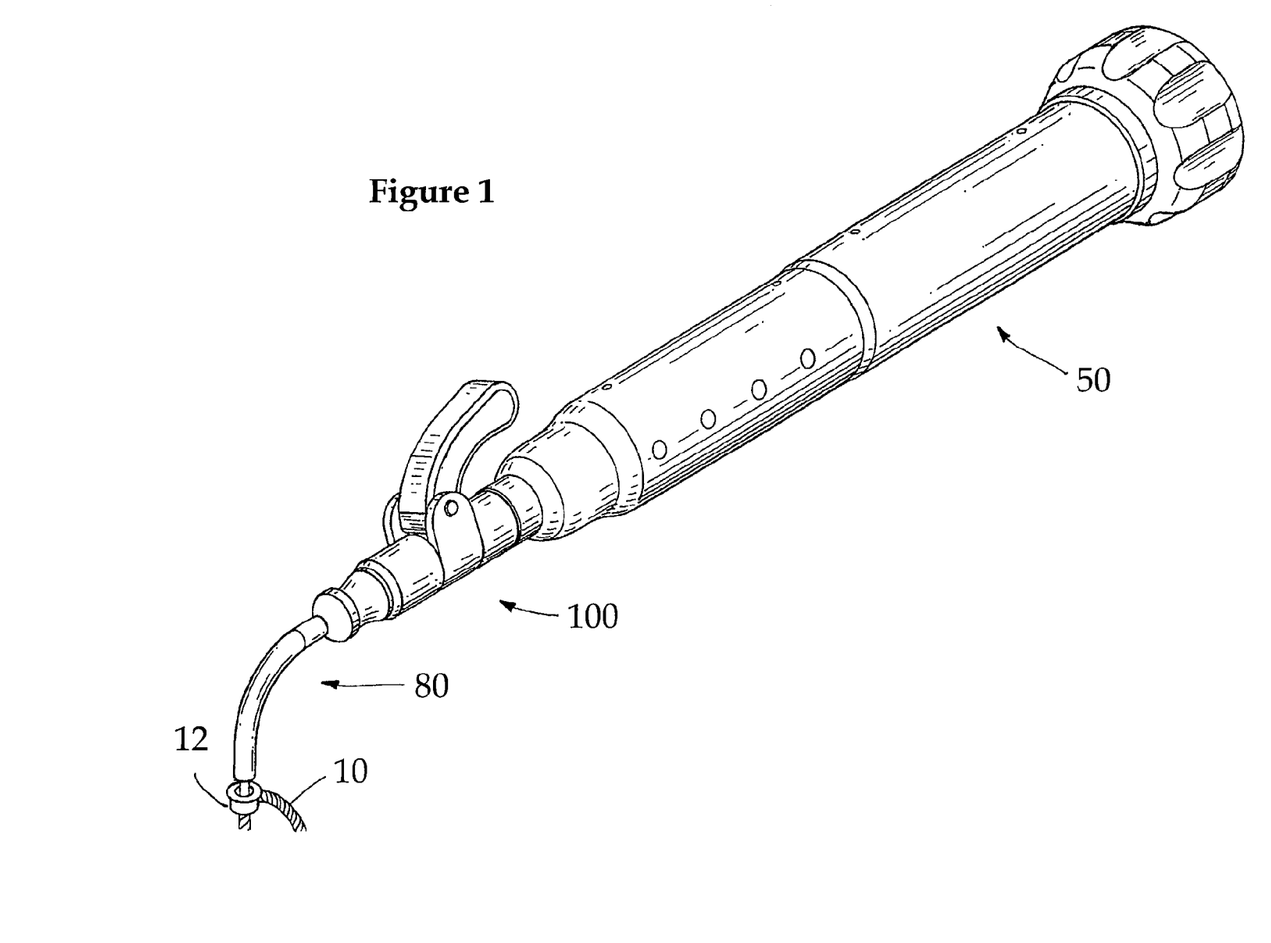
FIG. 1 is a plane view of an exemplary cable clamp according to the invention in use with a cable tensioning tool.

FIG. 1 illustrates an exemplary cable clamp 100 according to a preferred embodiment of the invention illustrated as part of a larger assembly that includes a tensioning tool 50 and a cable guide assembly 80. Although the invention will be described with reference to an exemplary cable clamp, it is not intended to be limited to devices for clamping cables, but is intended to encompass devices for clamping wires and other elongate members. Tensioning tool 50 provides a mechanism for applying a measured tension to cable 10, which extends through a "top hat" crimp 12 to form a loop for orthopedic fastening. As is known in the art, one end of the cable 10 is secured around the outside of the crimp and the other end extends through a bore in the crimp, through cable guide assembly 80, through a bore in cable clamp 100 and into the tensioning tool where it is gripped by a mechanism, the details of which are not important for an understanding of the invention.

Cable guide assembly 80 functions to prevent abrupt bending in the cable during application of the tensioning force to the cable 10. As will be apparent to those of ordinary skill, cable 10 will typically be one of a number of cables used as loop fasteners in a particular surgical application. Clamp 100, the details of which will be explained below, provides a means for temporarily clamping the cable 10 after a measured tension has been applied thereto. After initially tensioning cable 10, a surgeon will typically remove the tensioning tool 50 from engagement with the clamping device and cable 10, and use the tensioning tool to apply tension to another cable fastener (not shown) used in the surgical application in conjunction with another clamp (not shown) for temporarily clamping the tensioned cable. After tensioning the other cable, the tension of cable 10 may be readjusted by engaging the cable with the tensioning tool and re-tensioning the cable 10. In this manner, the tensions of all cables used in the procedure may be optimized before the cables are semi-permanently affixed by deforming the crimp elements 12.

Figure 2:
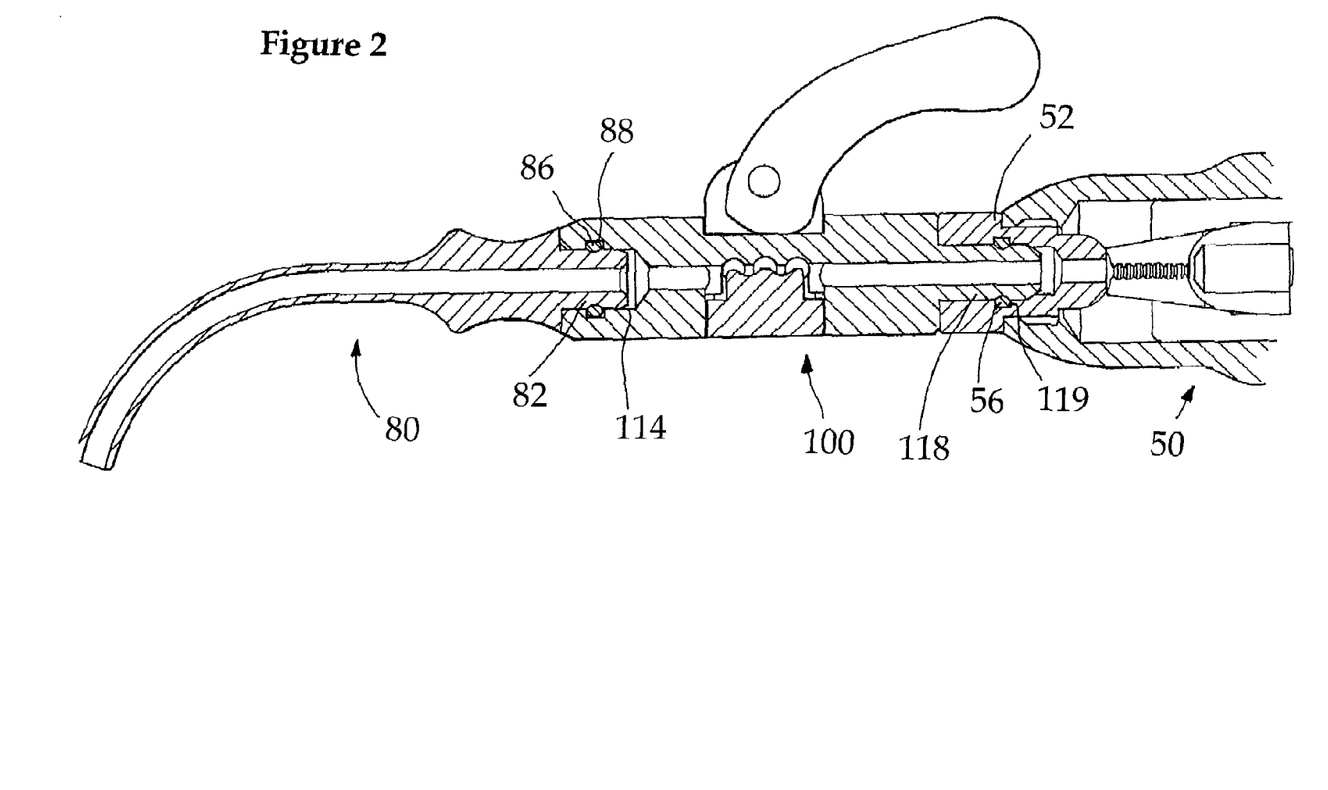
FIG. 2 is a cutaway of a cable clamp and cable tensioning tool illustrated in FIG. 1.

Referring additionally to FIG. 2, which is a partial section of the cable clamp 100, guide assembly 80 and tensioning tool 50, cable clamp 100 is secured to both tensioning tool 50 and cable guide assembly 80 using releasable connecting elements. The cable 10 (FIG. 1) has been omitted from this illustration for clarity. Guide assembly 80 includes a generally cylindrical guide barrel 82 which is received in a complementarily-shaped clamp socket 114. A deformable ring 86 is disposed in a guide barrel recess 84 and cooperates with an annular recess formed on the outer surface of guide barrel 82. Deformable ring 86 may be preferably formed of a coil spring element. As will be apparent to those of ordinary skill, deformable ring 86, in conjunction with guide barrel recess 84 and the annular recess on guide barrel 82, provides a releasable coupling that enables removal of guide 80 from clamp 100 with the application of a generally longitudinal force. A similar coupling is provided on an opposite end of cable clamp 100. Tensioning tool is provided with a tensioning tool socket 52, including an annular recess formed therein and retaining a deformable ring 56. Cable clamp 100 is provided with a clamp barrel 118 including an annular recess 119 which is releasably received in tensioning tool socket 52. Thus, guide 80, clamp 100 and tensioning tool 50 may be releasably assembled together.

Figure 3A:
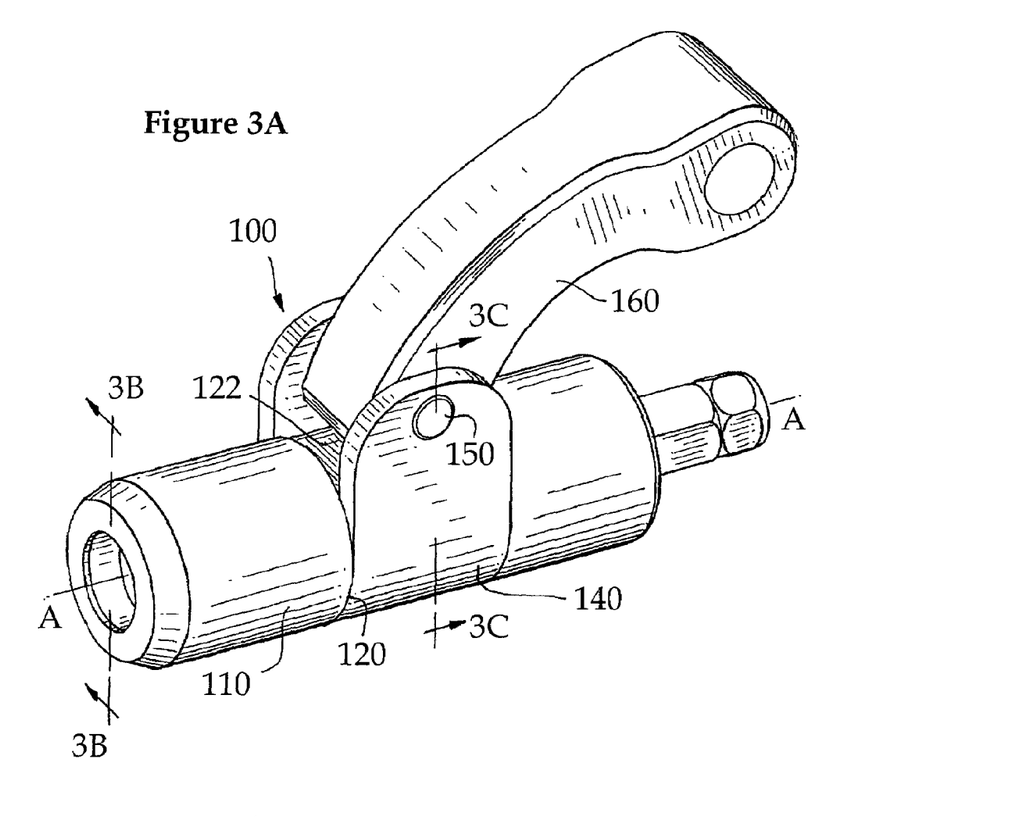
FIG. 3A is an isometric of an exemplary cable clamp according to the invention.
Figure 3B:
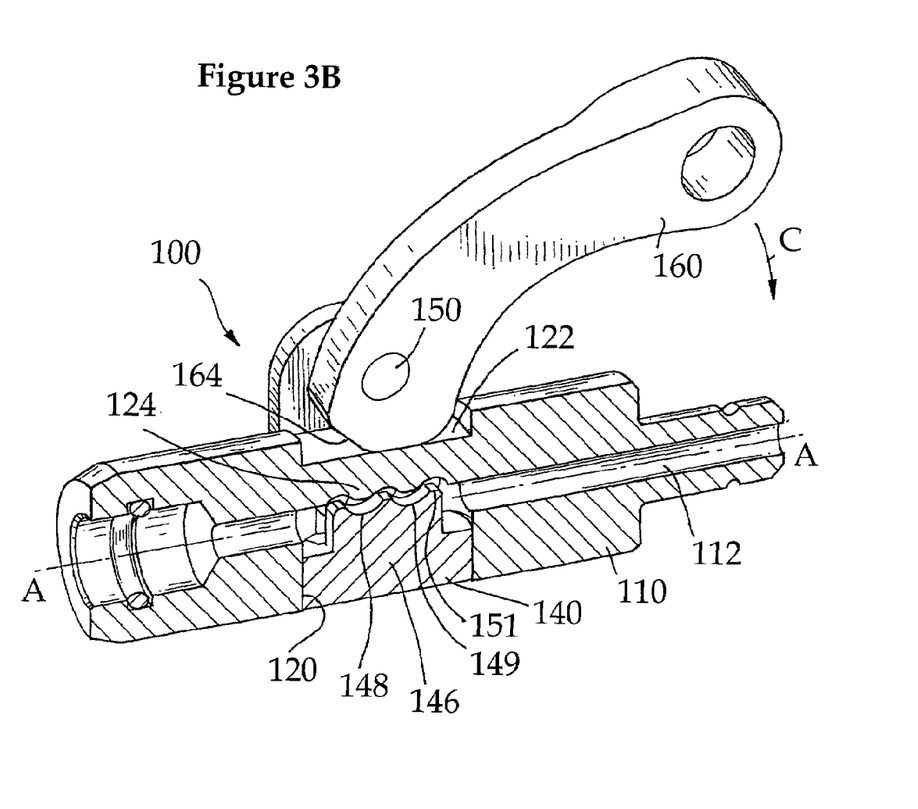
FIG. 3B is a section taken along a plane defined by line 3B-3B in FIG. 3A.

FIGS. 3A and 3B illustrate a cable clamp 100 according to a preferred embodiment of the invention. An exemplary cable clamp 100 is comprised of a generally cylindrical housing 110, which is provided with generally U-shaped saddle 140 movably mounted thereon. Saddle 140 is disposed within a saddle guide 120 formed in the housing 110. A cam lever 160 pivotably cooperates with saddle 140 by way of a pivot pin 150 retained within holes formed in the legs of the saddle 140. Cam lever 160 includes a cam surface 164 which engages a cam support surface 122 provided on the housing 110. As cam lever 160 is pivoted with respect to saddle 140 in a clamping direction, indicated by arrow C, saddle 140 is moved in a direction generally transverse to the longitudinal axis (A-A) of housing 110 to apply a clamping force to the cable (not shown) as will be described below.

Referring specifically to FIG. 3B, saddle 140 is provided with a generally rectangular-shaped saddle jaw 146 that defines an undulating saddle jaw surface 148. As illustrated and in order to simplify manufacture, saddle jaw surface 146 is formed from a series of curved recesses 149 separated by flat portions 151. The invention contemplates other jaw surface shapes, however, including serpentine jaw surfaces which include smooth transitions compared to the illustrated curved recesses 149 and flat portions 151. As will be recognized by those of ordinary skill, saddle jaw 146 does not necessarily have to be formed homogenously with saddle 140, but may be machined as a separate part and fastened to saddle 140 using conventional fastening techniques, such as welding or threaded fasteners. Saddle jaw 146 extends into the bore 112 of housing 110 for engaging a periphery of the cable (not shown in FIG. 3B). Saddle jaw 146 cooperates with a complementarily-shaped housing jaw 124 in order to form a generally undulating clamping space. The undulating surface of housing jaw 124 shown in FIG. 3B may be formed as a series of annular ribs within the housing bore 112.

Figure 3C:
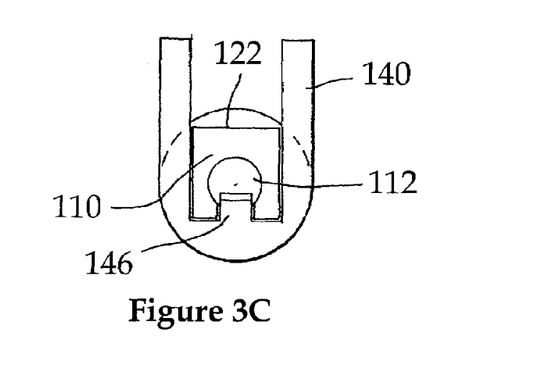
FIG. 3C is a section view taken along lines 3C-3C of FIG. 3A.

Referring additionally to FIG. 3C, saddle jaw 146 is disposed within a generally rectangular saddle jaw guide 150 formed in the housing 110 on a side opposite cam support surface 122. Saddle jaw 146 can therefore move within the saddle jaw guide 150 in a direction generally perpendicular to the housing bore axis.

As will be appreciated by those of ordinary skill, the movement of the cam lever 160 from a released position in the direction of arrow C (FIG. 3B) to a clamping position causes the cam surface 164 to move with respect to the cam support surface 122, thereby moving saddle 140 within saddle guide 120 in a direction substantially transverse to the longitudinal extent of bore 112 and into a clamping position. The housing jaw surface 124 and the saddle jaw surface 148 cooperate to redirect the cable from a substantially straight path to an undulating path when the saddle 140 is moved to a clamping position. It will be appreciated that the undulating surfaces of the saddle jaw and housing jaw increase the area of the cable to which the clamping force is applied. Thus, the amount of force that may be safely applied to a cable without risk of damage is increased compared to prior art clamping devices.

Figures 4, 5A:
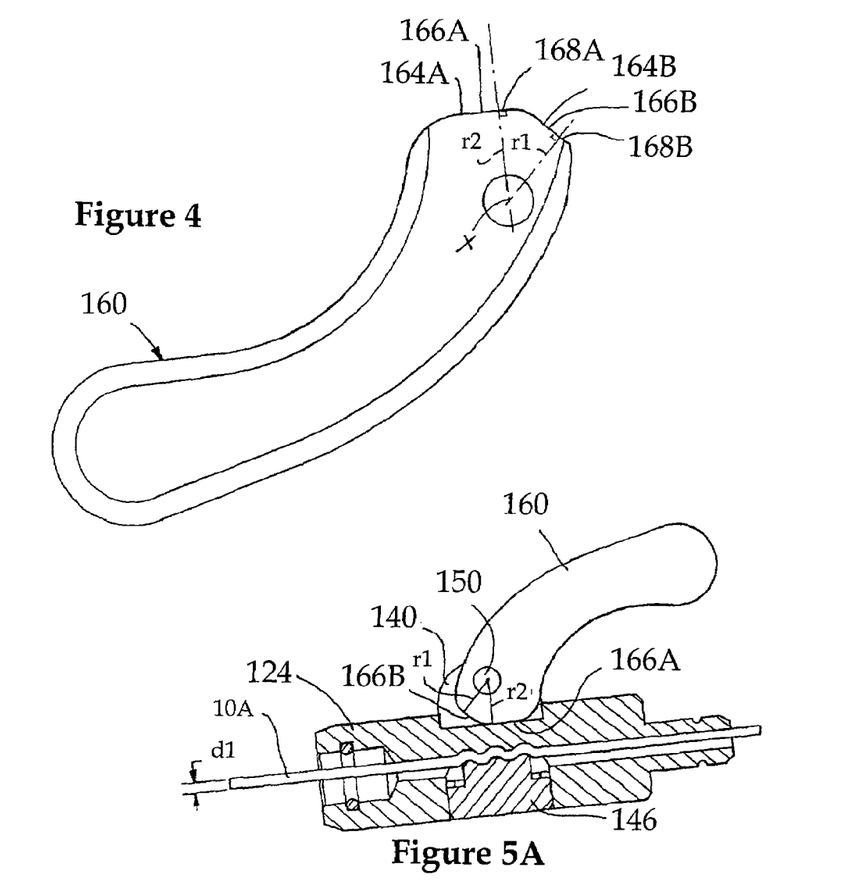
FIG. 4 is a side view of a cam lever according to a preferred embodiment of the present invention.
FIGS. 5A and 5B show cross-sections of an exemplary cable clamp according to the invention in two respective clamping positions for two different sized cables.

According to another aspect of the invention, cam lever 160 is provided with a multifaceted cam surface. Referring to FIG. 4, an exemplary cam surface 164 includes two facets: facet 164A and facet 164B, which each define a clamping position for clamping cables of two respective sizes, as will be explained below. Each facet 164A and 164B of the cam lever 160 is preferably provided as a substantially flat surface for engaging the cam support surface 122 on the housing 110. Each facet has associated with it a radial dimension r1 and r2 measured from the cam lever pivot axis (X). The radial dimensions are selected to provide optimum clamping force for corresponding cable sizes that may be used with the cable clamp. Preferably, cam surfaces 164A and 164B are provided with respective flat portions that extend on both sides of respective radial lines r1 and r2 to facilitate the positive locking aspects of the invention. That is, cam surface 164A includes a first flat portion 166A to the left of the point where radial line r2 intersects the cam surface 164A. Cam surface 164A also includes a second, smaller flat portion 168A that extends, for example for 0.025 inches, to the left of the point were radial line r2 intersects cam surface 164A. Cam surface 164B is provided with similar flat surface portions 166B and 168B. The two flat surface portions extending on both sides of the radial lines r1 and r2 (the radial lines also being perpendicular to the respective cam surfaces 164B and 164A) provide for stable locking positions of the cam lever 160 and positive tactile indication that the desired locking position has been reached.

Figure 5B:
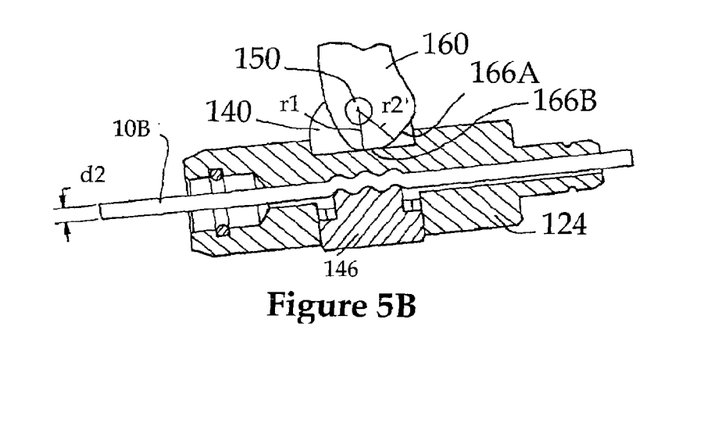

FIGS. 5A and 5B illustrate a clamp according to a preferred embodiment of the present invention being used with two different sized cables. As shown in FIG. 5A, a first cable 10A having a lateral dimension d1 is clamped between housing jaw 124 and saddle jaw 146 and cam lever 160 is positioned at a first clamping position. In the first clamping position, saddle jaw 146 and housing jaw 124 are disposed a predetermined and optimum distance from one another to provide a maximum safe clamping force to the first-sized cable 10A. Referring now to FIG. 5B, in accordance with the invention, the cable clamp 100 can be used to efficiently and safely clamp a second cable 10B of a second lateral dimension d2. As will be apparent, by virtue of the first radial dimension r1 of the cam lever 160, saddle jaw 146 is disposed further from housing jaw 124 than in the clamping position illustrated in FIG. 5A. Saddle jaw 146 is disposed an optimum distance from housing jaw 124 to provide the maximum safe clamping force to cable 10B.

As will be recognized by those of ordinary skill, the clamp of the invention advantageously applies a clamping force to the cable without direct contact between the lever and the cable, thereby preventing damage from abrasion and shear forces. Clamping force is applied through the saddle, which applies a lateral force against the cable surface and redirects the cable into an undulating or non-linear path defined between the housing jaw and saddle jaw. Thus, the potential for damage to the cable surface is reduced compared to prior art cable clamps. Moreover, less clamping force is required since with cable tension, the cable attempts to straighten and consequently applies normal forces to the obstructing internal surfaces of the clamp. These cable tension induced normal forces reduce the normal forces required to be generated by the clamp body through action of the lever.

It will also be recognized that clamping devices in accordance with the invention may be used to clamp different sized cables, without refitting parts or clamping jaws with new dimensions. Moreover, the clamping devices according to the invention provide for positive tactile determination as to when the cam lever 160 has been moved to one of a plurality of clamping positions.

FIGS. 6-12 will be understood to show additional embodiments and aspects of the present invention. Referring now to FIGS. 3A-12 as a group it is apparent that the present invention achieves advantages over the prior art by employing a lever in cooperation with a lever interface surface for moving an engaging surface of at least one clamping member relative to a cable housing and clamping an elongate member therein. FIGS. 3A-12 as a group show that the present invention contemplates a variety of clamping members movably mounted relative to a cable housing. The invention also contemplates a variety of levers and lever interface surfaces for moving the clamping member or members and for providing a surgeon with a tactile indication that a predetermined clamping force has been applied to the elongate member. The present invention further contemplates a variety of engaging surfaces designed to securely engage the elongate member by spreading the clamping force over a greater area of the elongate member than accomplished in the prior art, while increasing the normal force clamping the elongate member without damaging the elongate member. Additional embodiments and aspects of the invention are described in detail below.

Figure 6:
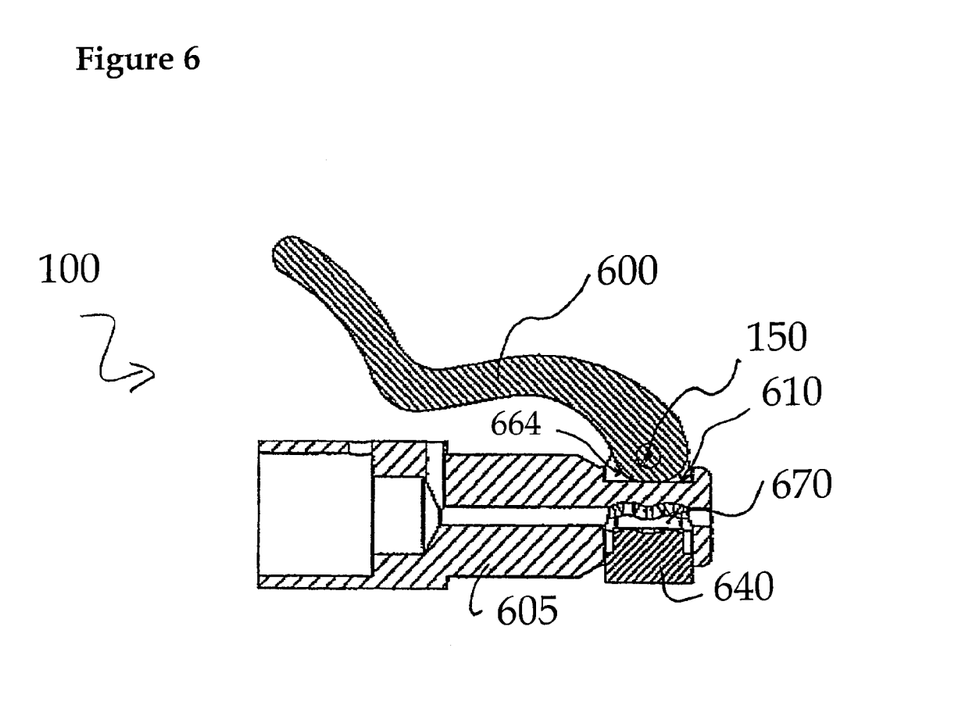
FIG. 6 is a cross-section view of a clamping device with a lever interface surface on the housing.

FIG. 6 illustrates a cross-section of clamp 100 in accordance with another embodiment of the present invention. As shown, oblong face 664 of lever 660 cooperates with lever interface surface 610. As lever 660 is pivoted about pivot pin 150, saddle member 640 moves relative to housing 605 in a direction that is generally transverse to the elongate member. Engaging surface 670 is formed on saddle member 640, housing 605 or on both saddle member 640 and housing 605 to engage at least a portion of the periphery of the elongate member. Engaging surface 670 is formed in any variety of shapes so as to engage a portion of the periphery of the elongate member. In particular, engaging surface 670 can be non-linear along at least a portion of its lengthwise cross-section, and/or concave along at least a portion of its widthwise cross-section. In these two exemplary forms, engaging surface 670 respectively serves to redirect the elongate member into a non-linear path and to cup a length of the elongate member at the point of clamping. Engaging surface 670 also serves to increase the normal force for clamping the elongate member, without damaging the elongate member.

Figure 7A:
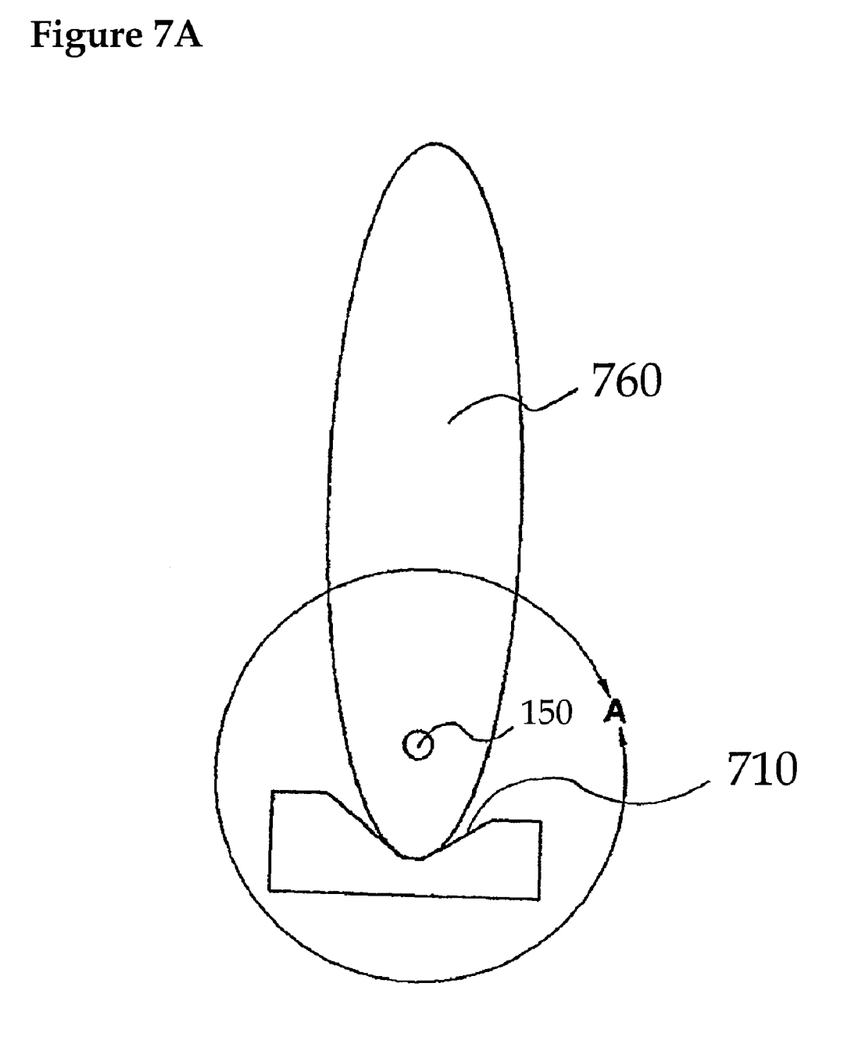
FIGS. 7A and 7B are detail views of a lever and lever interface cam surface according to the invention.
Figure 7B:
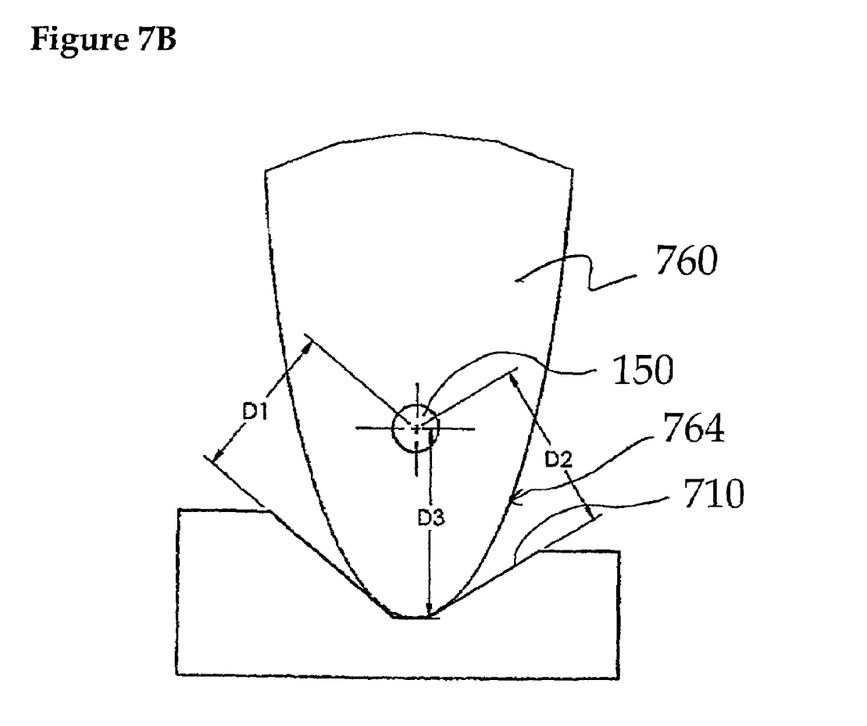

FIGS. 7A and 7B show a cross-sectional view of a clamp to illustrate details of oblong lever face 764 on lever 760 cooperating with nonplanar cam surface 710.

Lever face 764 may also include one or more facets to further cooperate with nonplanar cam surface 710. Nonplanar cam surface 710 has at least two discrete surface areas corresponding to locking positions of lever 760. These locking positions correspond to optimal clamping of the elongate member, and provide the surgeon with tactile indications of positive clamping force applied to the elongate member. Cam surface 710 is representative of nonplanar lever interface surfaces that can be formed on various embodiments of the clamping device. Nonplanar cam surfaces like cam surface 710 can be formed on the clamping device housing or on a clamping device platen to cooperate with a lever like lever 760. Thus, referring now to both FIGS. 6 and 7B, one can appreciate that cam surface 710 can replace lever interface surface 610 to cooperate with lever 660. In this aspect of the invention, the nonplanar housing cam surface can be modified to include a wide variety of raised or lowered surface dimensions for clamping elongate members of varying diameters.

Figure 8:
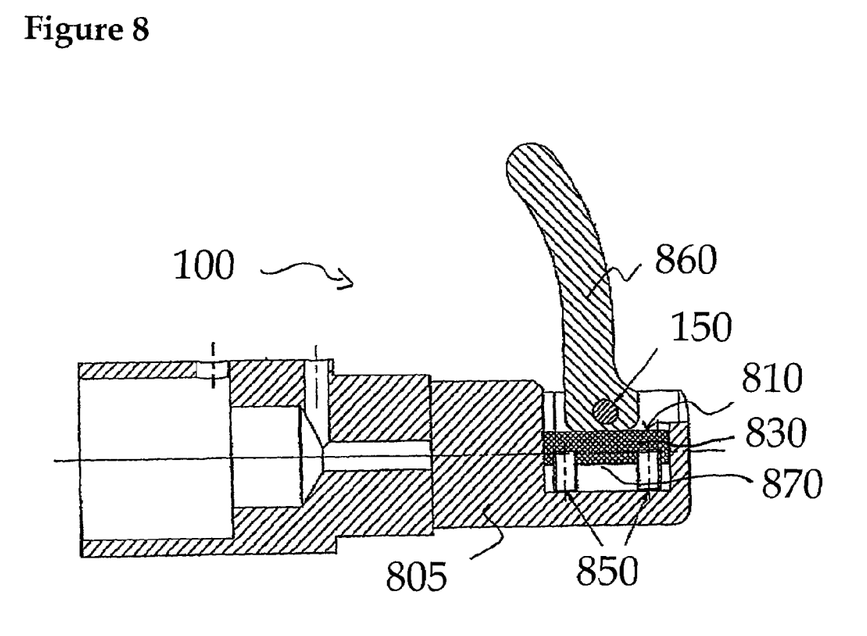
FIG. 8 shows a cross-section of a clamping device with a platen according to the invention.

In still other embodiments of the present invention, the lever may cooperate with other clamping members to achieve clamping of an elongate member. For example, FIG. 8 shows a cross-section of clamping device 100 with a platen 830. In this example of the invention, lever 860 is attached to housing 805 with pivot pin 150. Lever 860 can be rotated on pivot pin 150 to cooperate with lever interface surface 810 on platen 830, and thereby move the platen relative to the housing in a direction that is generally transverse to the elongate member. Referring now to both FIGS. 6 and 8, it is apparent that engaging surface 870 is analogous to engaging surface 670 and can be formed and attached in similar ways to accomplish similar advantages of engaging a periphery of the elongate member. Referring now to FIGS. 7B and 8, one can appreciate that cam surface 710 can replace lever interface surface 810. In this aspect of the invention, the discrete surface areas of the platen cam surface can be modified for clamping elongate members of varying diameters. One or more springs 850 can be added to suspend platen 830, for example, to keep the cable bore clear of the platen or saddle member whenever the lever is not activated and moved into a clamping position, thereby allowing an elongate member to be introduced into the device. Springs 850 may be any variety of coil springs, leaf springs, resilient chemical compounds or the like.

Figure 9:
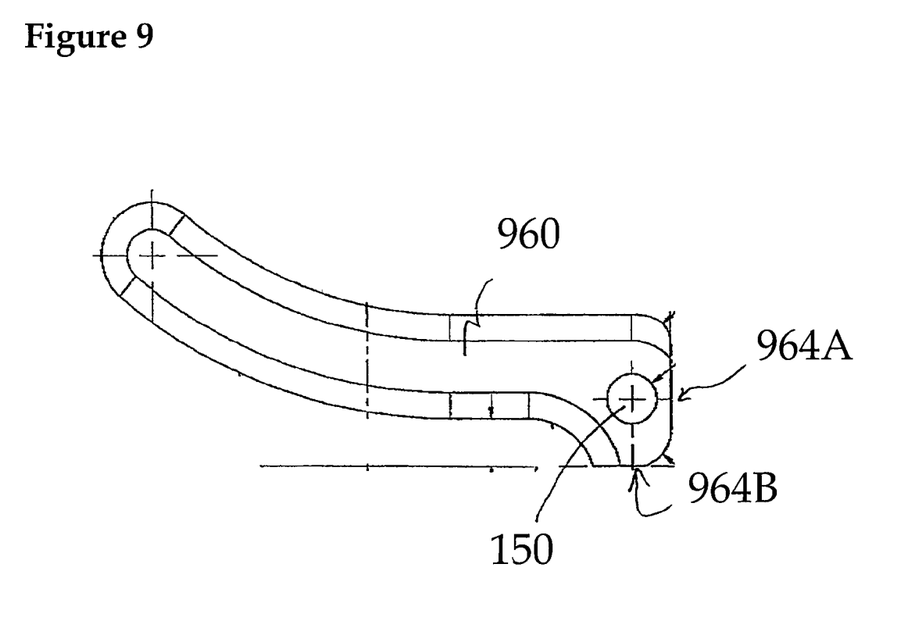
FIG. 9 shows a detail of a lever with lever cam facets according to the invention.

FIG. 9 shows a detail of lever 960 with lever cam facets 964A and 964B. These cam facets cooperate with the lever interface surface of the invention and provide locking positions corresponding to optimal clamping of the elongate member. The radial dimension from pivot pin 150 to cam facet 964A and 964B can be varied to accommodate varying diameter elongate members within the device, while maintaining optimal clamping forces.

Figure 10:
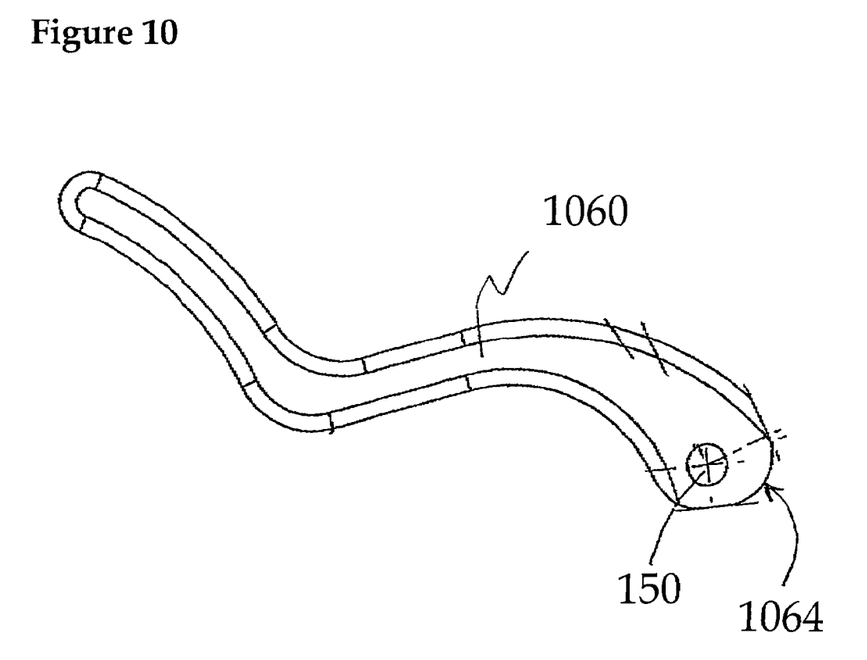
FIG. 10 shows a detail of a lever with an oblong lever face according to the invention.

FIG. 10 depicts a detail of lever 1060 with oblong face 1064. Oblong face 1064 can be defined as a single lobe, a tear-drop shaped cam or a generally oblong surface for cooperating with the lever interface surface of the invention. Referring now to both FIGS. 7B and 10, one can appreciate that oblong face 1064 can be one of a variety of generally oblong shapes designed to cooperate with a housing or platen cam surface like cam surface 710 and define predetermined clamping positions. The radial dimensions from pivot pin 150 to points along oblong face 1064 can be varied to accommodate varying diameter elongate members within the device, while maintaining optimal clamping force. Referring now to FIGS. 2-12 as a group, it is apparent that the invention contemplates a variety of levers and lever interface surfaces for selectively moving a saddle member or platen relative to the cable housing.

Figure 11:
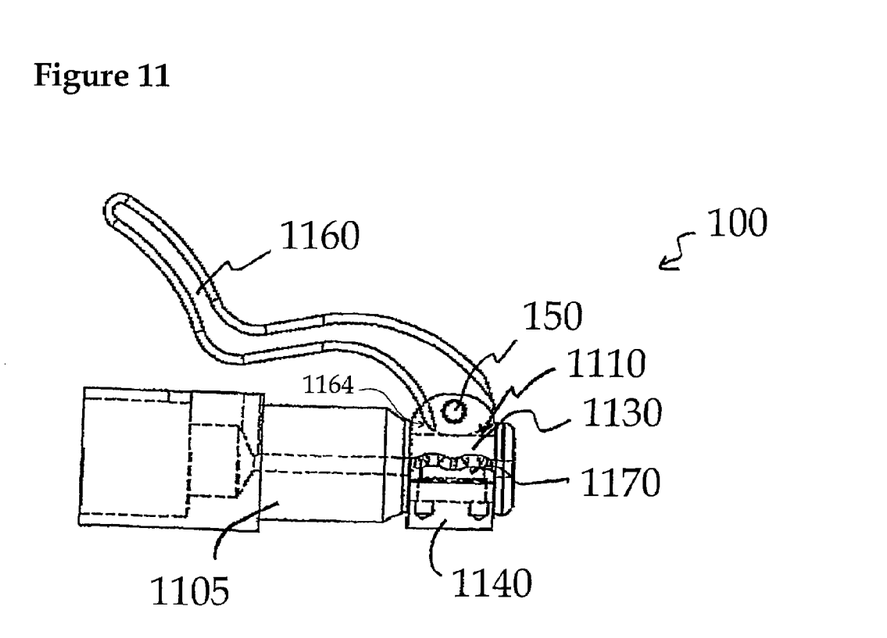
FIG. 11 shows a partial cross-section of a clamping device with both a saddle member and a platen according to the invention.

Still other embodiments of the invention contemplate that a combination of clamping members can be employed to cooperatively clamp an elongate member. FIG. 11 shows a partial cross-section of clamping device 100 employing both a platen 1130 and a saddle member 1140. In this example of the invention, lever 1160 is attached to saddle member 1140 with pivot pin 150. Platen 1130 and saddle member 1140 are movably mounted relative to housing 1105 to clamp an elongate member within the housing when a surgeon rotates lever 1160. Referring to FIGS. 7B, 8 and 11, lever face 1164 of lever 1160 can be understood to be a faceted cam surface or a generally smooth, oblong lobe cooperating with platen interface surface 1110. Continuing to refer to FIGS. 7B, 8 and 11, platen interface surface 1110 can be understood to be either a generally smooth surface, or a platen cam surface having at least two discrete surface areas. In this way, lever 1160 cooperates with platen 1130 to move the platen and the saddle member relative to the housing while providing the surgeon with positive tactile indications that predetermined clamping positions have been reached. As in other embodiments of the present invention, the dimensions of lever face 1164 and lever interface surface 1110 can be varied for the device to accommodate elongate members of varying dimensions.

Figure 12:
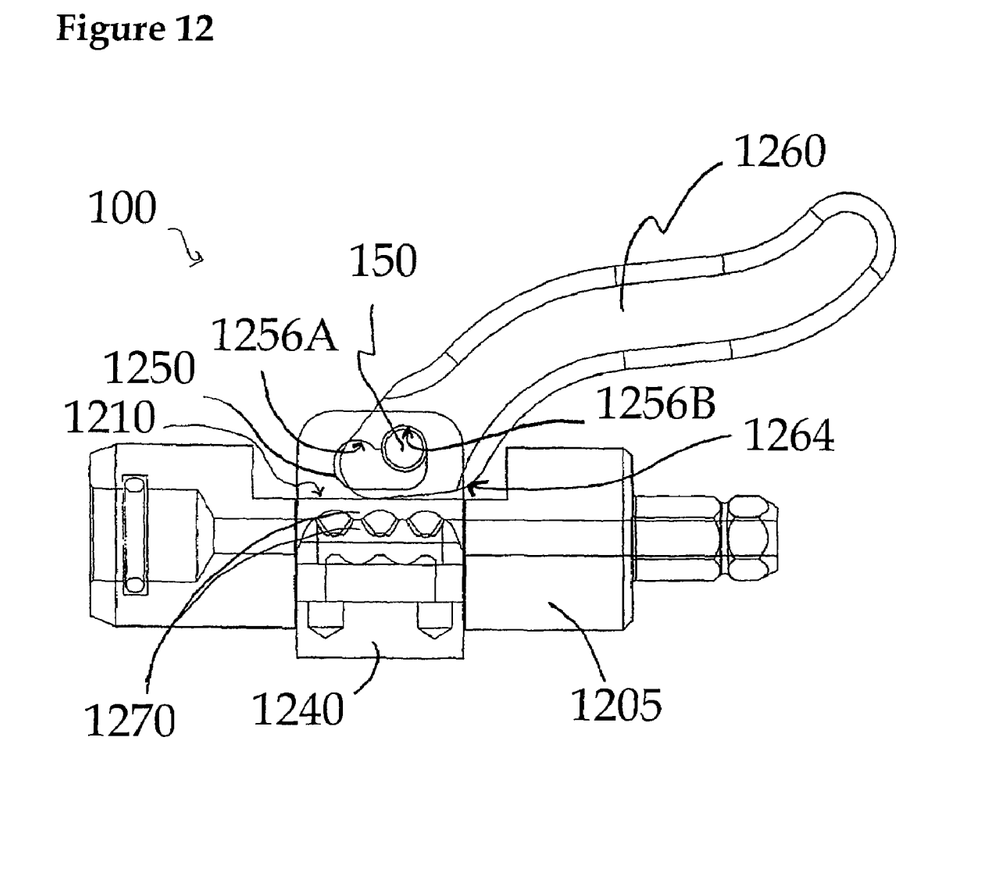
FIG. 12 shows a cross-section of a clamping device with a multi-position slot for the lever pivot according to the invention.

In still other embodiments of the invention, the lever can be attached to pivot from at least two different positions, thereby further allowing the invention to accommodate elongate members of varying diameters. FIG. 12 shows a cross-sectional view of clamping device 100 with lever 1260 mounted in slot 1250 of saddle member 1240. Slot 1250 includes a first position 1256A and a second position 1256B for receiving pivot pin 150. Lever 1260 can be moved to pivot from position 1256A or 1256B to accommodate elongate members of different sizes between engaging surfaces 1270. It will be understood that slot positions 1256A and 1256B can be varied, and that additional slot positions can be included, depending on the device's intended application. It will also be understood that slot 1250 can be formed in lever 1160 and pivot pin 150 can be secured to saddle member 1240 or housing 1205. Referring now to FIGS. 5A-12 as a group, it is apparent that the present invention contemplates use of a slot like slot 1250 with a variety of levers like lever 1260. Further, it is apparent that the invention contemplates a variety of lever surfaces 1264 able to cooperate with a variety of lever interface surfaces 1210 to move an engaging member like saddle member 1240 relative to housing 1205. In this way, engaging surfaces 1270 can be selectively moved to engage a periphery of an elongate member.

Although embodiments of this invention have been described hereinabove in some detail, it should be appreciated that a variety of other embodiments will be readily available to persons utilizing the invention for a specific end use. The descriptions above are not intended to be limiting on this invention, but are merely illustrative of the invention. Other products, apparatus and methods incorporating modifications or changes to that which has been described herein are equally included within this application. Additional objects, features and advantages of the present invention will become apparent by referring to the above description of the invention in connection with the accompanying drawings.

We claim:

1. An apparatus for tensioning and clamping an elongate member, the apparatus comprising:

a housing having a longitudinal axis and a throughbore extending longitudinally therethrough for receiving the elongate member therethrough;

a clamping member movably mounted to the housing for being shifted in a direction generally normal to the housing longitudinal axis;

a cam lever that cooperates with the clamping member and having a release position with the clamping member spaced from the elongate member and a clamp position with the clamping member engaged with the elongate member in the housing throughbore;

an undulating surface of at least one of the housing and the clamping member having surface portions that extend transversely to the housing longitudinal axis and which engage the elongate member with the cam lever shifted to the clamp position so that the clamped elongate member has a substantially matching undulating configuration in engagement therewith; and a tensioning tool coupled to the housing for receiving the elongate member therein and applying tension thereto along the housing longitudinal axis, so that with the cam lever in the clamp position, the tension in the elongate member will be in a direction transverse to the undulating surface portions to permit normal clamping forces that are generated by shifting the clamping member normal to the housing longitudinal axis to be reduced when the cam lever is shifted from the release position to the clamp position for clamping the elongate member in the housing throughbore.

2. The apparatus of claim 1 wherein both of the housing and the clamping member have an undulating surface that are complimentary to each other.

3. The apparatus of claim 1 wherein at least one of the housing, the clamping member, and the cam lever includes a lobe-shaped cam surface or a multifaceted cam surface at a cam interface between the housing and one of the clamping member and the cam lever to allow varying diameter elongate members to be clamped in the housing throughbore.

4. The apparatus of claim 1 wherein the clamping member is a saddle member having a generally U-shaped body portion including a pair of legs, wherein the cam lever fits between the legs of the U-shaped saddle body to be pivotally connected thereto.

5. The apparatus of claim 4 wherein the U-shaped saddle body has a lower base portion interconnecting the legs and having the undulating surface formed thereon so that pivoting the cam lever shifts the saddle member undulating surface into clamping engagement with the elongate member extending through the housing throughbore.

6. The apparatus of claim 1 wherein the clamping member is a platen adjacent the housing throughbore and biased into engagement with the cam lever in the release position to keep the platen from interfering with insertion of the elongate member through the throughbore.

7. The apparatus of claim 1 wherein the clamping member comprises a pair of clamping members that are shifted toward each other in a direction normal to the housing longitudinal axis to clamp the elongate member in the housing throughbore.

8. The apparatus of claim 7 wherein the pair of clamping members comprises a U-shaped saddle member and a platen.

9. The apparatus of claim 1 further comprising an arcuate cable guide assembly having an arcuate bore and coupled to a front end of the housing so that the arcuate bore and housing throughbore are aligned at the coupling therebetween for receiving the elongate member through the arcuate bore and the housing throughbore to keep the elongate member from abruptly bending as the elongate member exits the housing throughbore at the housing front end.

10. The apparatus of claim 1 wherein the clamping member includes a slot opening, and the cam lever is pivotally mounted to the clamping member in the slot opening with the slot opening being sized to allow the cam lever to be selectively adjusted between at least a first pivotal position and a second pivotal position spaced apart from each other in the slot opening so that different diameters of elongate members can be clamped in the housing throughbore depending on the selected first or second pivotal position of the cam lever.

11. A method of securing a cable to a bone, the method comprising:

connecting the cable to a bone;

inserting the cable into a clamping bore of a clamping tool to extend axially therethrough along an elongate axis extending through the clamping bore;

coupling a tensioning tool to the clamping tool;

applying a tensioning force to the cable with the tensioning force applied axially along the axis of the clamping tool bore using the tensioning tool;

applying a clamping force to the cable in the clamping tool bore using the clamping tool;

engaging the cable with clamping surface portions of the clamping tool that extend transverse to the clamping tool bore axis as the clamping force is applied to the cable;

bending the cable extending through the clamping tool bore with the clamping surface portions engaged therewith so that the axial tensioning force applied to the cable draws bent portions thereof tightly against the transversely extending clamp surface portions; and removing the tensioning tool from the clamping tool.

12. The method of claim 11 wherein the cable is connected to a bone by looping the cable about the bone.

13. The method of claim 11 wherein engaging the cable with the transverse clamping surface portions and bending the cable in the clamping tool bore includes reconfiguring the axially extending cable in the clamping bore to extend through the clamping tool bore in an undulating path.

* * * * *